(12) United States Patent
Jain et al.

(10) Patent No.: US 9,725,394 B2
(45) Date of Patent: Aug. 8, 2017

(54) COMPOSITION FOR PREPARING TEREPHTHALIC ACID

(71) Applicant: Reliance Industries Limited, Mumbai (IN)

(72) Inventors: Suresh Shantilal Jain, Palava (IN); Pavankumar Aduri, Palava (IN); Parasu Veera Uppara, Mumbai (IN); Prashant Sudhakar Tangade, Thane (IN)

(73) Assignee: RELIANCE INDUSTRIES LIMITED (IN)

( * ) Notice: Subject to any disclaimer, the term of this patent is extended or adjusted under 35 U.S.C. 154(b) by 0 days.

(21) Appl. No.: 14/787,764

(22) PCT Filed: Apr. 17, 2014

(86) PCT No.: PCT/IN2014/000245
§ 371 (c)(1),
(2) Date: Oct. 28, 2015

(87) PCT Pub. No.: WO2014/181345
PCT Pub. Date: Nov. 13, 2014

(65) Prior Publication Data
US 2016/0083325 A1    Mar. 24, 2016

(30) Foreign Application Priority Data
Apr. 30, 2013    (IN) .......................... 1565/MUM/2013

(51) Int. Cl.
*C07C 51/265*    (2006.01)
(52) U.S. Cl.
CPC .................................. *C07C 51/265* (2013.01)
(58) Field of Classification Search
CPC .................................................. C07C 51/265
See application file for complete search history.

(56) References Cited

U.S. PATENT DOCUMENTS

| | | | |
|---|---|---|---|
| 2,833,816 | A | 5/1958 | Saffer et al. |
| 6,153,790 | A | 11/2000 | June et al. |
| 6,355,835 | B1 | 3/2002 | Kulsretha et al. |
| 7,094,925 | B2 | 8/2006 | Earle et al. |
| 2009/0326265 | A1 | 12/2009 | Hashmi et al. |
| 2010/0174111 | A1 | 7/2010 | Rogers et al. |
| 2012/0004449 | A1 | 1/2012 | Bhattacharyya et al. |
| 2012/0004450 | A1 | 1/2012 | Bhattacharyya et al. |
| 2012/0004451 | A1 | 1/2012 | Bhattacharyya et al. |
| 2012/0004454 | A1 | 1/2012 | Bhattacharyya et al. |
| 2012/0004455 | A1 | 1/2012 | Bhattacharyya et al. |

FOREIGN PATENT DOCUMENTS

| | | |
|---|---|---|
| WO | 2012-012047 A2 | 1/2012 |
| WO | WO2013010133 * | 7/2013 |

OTHER PUBLICATIONS

ISA/IN, International Search Report for Int'l Appln No. PCT/IN2014/000245, Sep. 15, 2014, 3 pages.

* cited by examiner

*Primary Examiner* — Paul A Zucker
*Assistant Examiner* — Mark Luderer
(74) *Attorney, Agent, or Firm* — Fish IP Law, LLC

(57) ABSTRACT

The present disclosure provides a composition for preparing terephthalic acid; said composition comprises p-Toluic acid in an amount of 0.05% to 4% with respect to the total mass of the composition; at least one catalyst in an amount of 0.02% to 2.5% with respect to the total mass of the composition; at least one ionic liquid in an amount of 0.04% to 50% with respect to the total mass of the composition; at least one carboxylic acid solvent; and p-xylene. The present disclosure also provides a process for preparing terephthalic acid.

9 Claims, No Drawings

COMPOSITION FOR PREPARING TEREPHTHALIC ACID

FIELD

The present disclosure relates to a composition for preparing terephthalic acid. The present disclosure also relates to a process for the preparation of terephthalic acid.

BACKGROUND

Terephthalic acid is an organic compound with formula $C_6H_4(COOH)_2$. This colourless solid is a commodity chemical, used as a precursor for polyester PET, used to make clothing and plastic bottles. World production in 1970 was around 1.75 million tonnes. By 2006, global purified terephthalic acid (PTA) demand exceeded 30 million tonnes. There is a smaller, but nevertheless significant, demand for terephthalic acid in the production of polybutylene terephthalate and several other engineering polymers. In the research laboratory, terephthalic acid is a component for the synthesis of metal-organic frameworks. Due to the wider applications of terephthalic acid, many methods for its manufacturing and purification have been developed in recent years.

Some of the prior art documents which disclose the processes for the synthesis of terephthalic acids are as follows.

U.S. Pat. No. 2,833,816 suggests a process for producing aromatic carboxylic acid such as terephthalic acid by oxidation of aromatic compounds such as para-xylene at 120 to 275° C. in the presence of acetic acid, metal catalyst and a bromine source. During the oxidation reaction, the intermediates that are formed are p-toulic acid and 4-carboxy-benzaldehyde (4-CBA). Para-toulic acid remains in soluble state in the solvent. However, 4-CBA co-crystallizes with the product due to its similar crystal structure. Terephthalic acid which contains 4-CBA is typically termed as crude terephthalic acid. The crude terephthalic acid (CTA) containing 4-CBA is undesirable in producing polyester as it acts as a chain terminating agent during polymerization. Hence CTA is required to be further purified by additional steps.

U.S. Pat. No. 7,094,925 mentions a process for the oxidation of an alkyl-aromatic compound which comprises admixing the aromatic compound with an oxidizing agent or sulfur compound in the presence of an ionic liquid and a nitrogen oxyacid species. Ionic liquid used in the process comprises an organic anion selected from the group consisting of trifluoroacetate, acetate, methanesulfonate, and combinations thereof or an anion based on sulfur, nitrogen, phosphorous, silicon, selenium, tellurium, arsenic, antimony, bismuth, or oxoanions of a metal. The process mentioned in U.S. Pat. No. 7,094,925 is carried out under Bronsted acidic conditions.

US2009/0326265 suggests the use of 1-ethyl-3-methylimidazolium bromide as a bromine source during oxidation. The use of molecular bromine typically releases free bromine which causes corrosion to equipment.

In U.S. Pat. No. 6,355,835, the use of methylethlyketone (MEK) as a promoter to replace the bromine source is suggested. However, the process in U.S. Pat. No. 6,355,835 needs a large quantity of catalyst. Another disadvantage of the process is that the organic promoter may undergo oxidation at the process operating conditions, further complicating purification steps.

U.S. Pat. No. 6,153,790 suggests the utilization of a catalyst system which is a combination of cobalt and zirconium species for the preparation of aromatic carboxylic acids.

US2010/0174111 suggests a process for providing crystalline terephthalic acid comprising: a) providing a composition comprising terephthalic acid and one or more ionic liquids; and b) combining the composition of step (a) with a non-solvent (water), thereby crystallizing terephthalic acid.

US20120004449 suggests a process for oxidizing an alkyl-aromatic compound which comprises forming a mixture comprising the alkyl-aromatic compound, a solvent, a bromine source, and a catalyst; and contacting the mixture with an oxidizing agent to produce a solid oxidation product comprising at least one of an aromatic aldehyde, an aromatic alcohol, an aromatic ketone, and an aromatic carboxylic acid; wherein the solvent comprises a carboxylic acid having from 1 to 7 carbon atoms and an ionic liquid selected from the group consisting of an imidazolium ionic liquid, a pyridinium ionic liquid, a phosphonium ionic liquid, a tetra alkyl ammonium ionic liquid, and combinations thereof.

US2012/0004450 suggests a process for producing terephthalic acid from para-xylene which comprises forming a mixture comprising the para-xylene, a solvent, a bromine source, and a catalyst; and oxidizing the para-xylene by contacting the mixture with an oxidizing agent to produce a solid oxidation product comprising terephthalic acid, 4-carboxybenzaldehyde, and para-toluic acid; wherein the solvent comprises a carboxylic acid having from 1 to 7 carbon atoms, a dialkyl imidazolium ionic liquid, and optionally water.

US2012/0004451 suggests a process for producing terephthalic acid from para-xylene which comprises forming a mixture comprising the para-xylene, a solvent, a bromine source, a catalyst and ammonium acetate; and oxidizing the para-xylene by contacting the mixture with an oxidizing agent to produce a solid oxidation product comprising terephthalic acid, 4-carboxybenzaldehyde, and para-toluic acid; wherein the solvent comprises a carboxylic acid having from 1 to 7 carbon atoms.

US2012/0004454 suggests a mixture for oxidizing an alkyl-aromatic compound comprising: the alkyl-aromatic compound, a solvent, a bromine source, and a catalyst; wherein the solvent comprises a carboxylic acid having from 1 to 7 carbon atoms and an ionic liquid selected from the group consisting of an imidazolium ionic liquid, a pyridinium ionic liquid, a phosphonium ionic liquid, a tetra alkyl ammonium ionic liquid, and combinations thereof.

The aforesaid documents focus on preparing terephthalic acid by oxidation of xylene in the presence of a catalyst, a solvent and a bromine source. The solvents utilized include acetic acid, water and ionic liquids.

These processes are not able to produce pure terephthalic acid. i.e. these processes are not able to reduce the formation of intermediates such as 4-carboxy-benzaldehyde. Therefore, these processes inherently require additional purification steps. Further, these processes utilize excess amount of bromine and metal catalyst.

Accordingly, it is desirable to develop a mixture which can undergo oxidation and produce terephthalic acid which is substantially free of intermediates such as 4-carboxy-benzaldehyde.

Objects

Some of the objects of the present disclosure which at least one embodiment herein satisfies are as follows:

It is an object of the present disclosure to provide a composition for the preparation of terephthalic acid.

It is another object of the present disclosure to provide a composition for the preparation of purified terephthalic acid, which is capable of reducing the formation of intermediates.

It is another object of the present disclosure to provide a simple, safe and cost effective process for the preparation of purified terephthalic acid.

Other objects and advantages of the present disclosure will be more apparent from the following description which is not intended to limit the scope of the present disclosure.

SUMMARY

In accordance with the present disclosure there is provided a composition for preparing terephthalic acid; said composition comprising:
- p-Toluic acid in an amount of 0.05% to 4% with respect to the total mass of the composition;
- at least one catalyst in an amount of 0.02% to 2.5% with respect to the total mass of the composition;
- at least one ionic liquid in an amount of 0.04% to 50% with respect to the total mass of the composition;
- at least one carboxylic acid solvent; and
- p-xylene,
- said composition when used in the preparation of terephthalic acid, results in the formation of 4-carboxybenzaldehyde (4-CBA) less than 2000 ppm of terephthalic acid.

The proportion of the ionic liquid to the carboxylic acid solvent can range between 1:1 and 1:20.

The ionic liquid can be at least one selected from the group consisting of alkyl ionic liquids and aryl alkyl ionic liquids.

The ionic liquid can comprise an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium; and an anion selected from the group consisting of chloride, bromide, fluoride, iodide, mesylate, tosylate, hydrogen sulfate, sulfate, alkyl sulfonate, phosphates, phosphonates, akyl phosphates, nitrates, nitrites, carbonates, acetates, bicarbonates, hydroxides and oxides.

The catalyst can comprise at least one metal compound, the metal being selected from the group consisting of cobalt, magnesium, chromium, copper, nickel, vanadium, iron, molybdenum, tin, cerium, zirconium, cesium and titanium.

The catalyst can be at least one selected from the group consisting of cobalt acetate, manganese acetate, cerium acetate, potassium acetate, cesium acetate, zirconium acetate, copper acetate, cobalt oxalate, manganese oxalate, cerium oxalate, potassium oxalate, cesium oxalate, zirconium oxalate and copper oxalate.

The composition can further comprise at least one bromine source selected from the group consisting of HBr, NaBr, KBr, $NH_4Br$, benzylbromide, monobromoacetic acid, di-bromo acetic acid, bromoacetyl bromide, tetrabromomethane and ethylene di-bromide.

In accordance with another aspect of the present disclosure there is provided a process for preparing terephthalic acid; said process comprising the following steps:
- preparing a composition comprising p-Toluic acid in an amount of 0.05% to 4% with respect to the total mass of the composition; at least one catalyst in an amount of 0.02% to 2.5% with respect to the total mass of the composition; at least one ionic liquid in an amount of 0.04% to 50% with respect to the total mass of the composition; at least one carboxylic acid solvent and p-xylene; and
- oxidizing said composition in the presence an oxidizing agent selected from the group consisting of oxygen and air, at a temperature of 100 to 250° C. and at a pressure of 10 to 60 bar to obtain terephthalic acid,
- the content of 4-carboxy-benzaldehyde (4-CBA) being less than 2000 ppm.

DETAILED DESCRIPTION

Conventionally terephthalic acid is produced by wet oxidation of para-xylene. In the process of wet oxidation, acetic acid is used as a solvent, cobalt and manganese acetates are used as catalysts and hydrogen bromide is used as a promoter.

Molecular species that are detected during the wet oxidation process of para-xylene are terephthalic acid as a main product (crude terephthalic acid), intermediates such as para-tolualdehyde, para-toluic acid, 4-carboxybenzhaldehyde and side products such as isophthalic acid, phthalic acid, meta or ortho-tolualdehyde, metaor ortho-toluic acid, 2 or 3-carboxybenzhaldehyde, 3 or 4-Bromo methyl benzoic acid, benzoic acid, trimelliticacids, trimesic acid, benzaldehyde, phthalaldehyde, ethylbenzaldehyde, methylstyrene, diphenic acid, 2-biphenyl carboxylic acid, hemi melitic acid, dimethyl terephthalate, methyl p-toulate, 3-hydroxy 4-methyl benzoic acid, terephthal aldehyde, styrene, phenol, toluene, benzene, ethylbenzene, methylethylbenzene, formaldehyde, 1,3-cyclopentadiene, indene, methylnaphthalene, anthracene, phenantrene, phenylacetylene, methylbiphenyl, diphenylbutane, naphthalene, and 4,4-dimethylbibenzyl, vinylacetylene. The intermediates form in large amount and eventually convert into crude terephthalic acid during the wet oxidation of para-xylene.

It is important that the product, intermediates and side-products remain in soluble state during the reaction for complete conversion. In the conventional process, terephthalic acid crystals formed during the oxidation trap some of intermediates such as 4-CBA. It is known that to produce PET from terephthalic acid, it is essential to have 4-CBA content as low as 100 ppm in terephthalic acid. Therefore, in the conventional process, the impure Terephthalic acid again needs to be subjected to hydrogenation to convert 4-CBA into p-toulic acid. Subsequently, p-toulic acid needs to be separated to obtain pure Terephthalic acid.

The inventors of the present disclosure have developed a starting mixture or composition which can be successfully oxidized to produce pure terephthalic acid.

Initially, the inventors of the present disclosure found that the ionic liquids can be used as a promoter as well as co-solvent. The ionic compounds solubilize the intermediates and side products during the oxidation. It is advantageous to keep these intermediates in dissolved form in the ionic compounds, as they can be further oxidized into the desired product during the manufacturing of terephthalic acid. Thus the concentration of intermediates can be reduced during the oxidation stage itself, thereby eliminating hydrogenation stage as against the conventional manufacturing process.

Further, the inventors of the present disclosure surprisingly found that incorporation of p-Toulic acid in the mixture or composition meant for oxidation significantly reduces the 4-carboxy-benzaldehyde (4-CBA) content in the terephthalic acid which in turn provides terephthalic acid in a highly pure form. Accordingly, the present disclosure provides a composition for preparing purified terephthalic acid, which essentially comprises p-Toluic acid. The effect of initial addition of p-Toluic acid is illustrated in the examples.

In accordance with the first aspect of the present disclosure there is provided a composition for preparing purified terephthalic acid. The composition contains p-Toluic acid in an amount of 0.05% to 4% with respect to the total mass of the composition; at least one catalyst in an amount of 0.02% to 2.5% with respect to the total mass of the composition; at least one ionic liquid in an amount of 0.04% to 50% with respect to the total mass of the composition; at least one carboxylic acid solvent; and p-xylene. The composition is adapted to reduce the formation of 4-carboxy-benzaldehyde (4-CBA) to less than 2000 ppm during the preparation of terephthalic acid.

In the present composition the proportion of the ionic liquid to the carboxylic acid solvent is maintained between 1:1 and 1:20.

In accordance with the present disclosure the ionic liquid is at least one selected from the group consisting of alkyl ionic liquids and aryl alkyl ionic liquids. The ionic liquid comprises an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium; and an anion selected from the group consisting of chloride, bromide, fluoride, iodide, mesylate, tosylate, hydrogen sulfate, sulfate, alkyl sulfonate, phosphates, phosphonates, akyl phosphates, nitrates, nitrites, carbonates, acetates, bicarbonates, hydroxides and oxides.

In one embodiment the ionic liquid is at least one aryl alkyl ionic liquid which includes but is not limited to 1-benzyl, 3-methyl imidazolium bromide; 1-benzyl, 3-methyl imidazolium chloride; 1-benzyl, 3-methyl imidazolium acetate; 1-benzyl, 3-methyl imidazolium methane sulfonate; 1-benzyl, 3-methyl imidazolium phosphate; Benzyl tributyl phosphonium bromide, Benzyl tributyl ammonium bromide; 1-phenyl, 3-methyl imidazolium chloride; 1-phenyl, 3-methyl imidazolium bromide; 1-phenyl, 3-methyl imidazolium acetate; 1-phenyl, 3-methyl imidazolium methane sulfonate; 1-phenyl, 3-methyl imidazolium phosphate; Phenyl tributyl phosphonium bromide; Phenyl tributyl ammonium bromide; 1,3-dibenzyl imidazolium chloride; 1,3-dibenzyl imidazolium bromide; 1,3-dibenzyl imidazolium acetate; 1,3-dibenzyl imidazolium methane sulfonate; and 1,3-dibenzyl imidazolium phosphate.

In another embodiment the ionic liquid is at least one alkyl ionic liquid which includes but is not limited to 1-butyl, 3-methyl imidazolium bromide; 1-butyl, 3-methyl imidazolium chloride; 1-butyl, 3-methyl imidazolium acetate; 1-butyl, 3-methyl imidazolium methane sulfonate; 1-butyl, 3-methyl imidazolium phosphate; 1-ethyl, 3-methyl imidazolium chloride; 1-ethyl, 3-methyl imidazolium bromide; 1-ethyl, 3-methyl imidazolium acetate; 1-ethyl, 3-methyl imidazolium methane sulfonate; 1-ethyl, 3-methyl imidazolium phosphate; Tetrabutyl phosphonium chloride; Tetrabutyl phosphonium bromide; Tetrabutyl phosphonium acetate; Tetrabutyl phosphonium methane sulfonate; Tetrabutyl phosphonium phosphate; Trihexyl Tetradecyl phosphonium chloride; Trihexyl Tetradecyl phosphonium bromide; Trihexyl Tetradecyl phosphonium acetate; Trihexyl Tetradecyl phosphonium decanoate; Tetrabutyl ammonium chloride; Tetrabutyl ammonium bromide; Tetrabutyl ammonium acetate; Tetrabutyl ammonium methane sulfonate; Tetrabutyl ammonium phosphate; Choline chloride; Choline bromide; choline acetate; and choline methane sulfonate.

In accordance with another embodiment of the present disclosure the ionic liquid employed in the composition comprises a combination of at least one alkyl ionic liquid and at least one aryl alkyl ionic liquid.

The catalyst employed in the composition comprises at least one metal compound, the metal being selected from the group consisting of cobalt, magnesium, chromium, copper, nickel, vanadium, iron, molybdenum, tin, cerium, zirconium, cesium and titanium. In one embodiment the catalyst is at least one selected from the group consisting of cobalt acetate, manganese acetate, cerium acetate, potassium acetate, cesium acetate, zirconium acetate, copper acetate, cobalt oxalate, manganese oxalate, cerium oxalate, potassium oxalate, cesium oxalate, zirconium oxalate and copper oxalate.

The composition of the present disclosure further comprises at least one bromine source selected from the group consisting of HBr, NaBr, KBr, $NH_4Br$, benzylbromide, monobromoacetic acid, di-bromo acetic acid, bromoacetyl bromide, tetrabromomethane and ethylene di-bromide.

In accordance with another aspect of the present disclosure there is provided a process for preparing purified terephthalic acid. The process involves the following steps:

In the first step a composition comprising p-Toluic acid in an amount of 0.05% to 4% with respect to the total mass of the composition; at least one catalyst in an amount of 0.02% to 2.5% with respect to the total mass of the composition; at least one ionic liquid in an amount of 0.04% to 50% with respect to the total mass of the composition; at least one carboxylic acid solvent and p-xylene is prepared. In the next step, the composition is oxidized in the presence an oxidizing agent selected from the group consisting of oxygen and air, at a temperature of 100 to 250° C. and at a pressure of 10 to 60 bar to obtain purified terephthalic acid. The carboxylic acid solvent employed is acetic acid. The process of the present disclosure is mainly characterized by 4-carboxy-benzaldehyde (4-CBA) content in terephthalic acid is less than 2000 ppm.

In accordance with the present disclosure the proportion of the ionic liquid to the carboxylic acid solvent is maintained between 1:1 and 1:20.

The process of the present disclosure further comprises a step of incorporating at least one bromine source selected from the group consisting of HBr, NaBr, KBr, $NH_4Br$, benzylbromide, monobromoacetic acid, di-bromo acetic acid, bromoacetyl bromide, tetrabromomethane and ethylene di-bromide in said composition.

In accordance with the present disclosure the ionic liquid comprises an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium; and an anion selected from the group consisting of chloride, bromide, fluoride, iodide, mesylate, tosylate, hydrogen sulfate, sulfate, alkyl sulfonate, phosphates, phosphonates, akyl phosphates, nitrates, nitrites, carbonates, acetates, bicarbonates, hydroxides and oxides. In one embodiment the ionic liquid is at least one selected from the group consisting of alkyl ionic liquids and aryl alkyl ionic liquids. In another embodiment the ionic liquid comprises a combination of at least one alkyl ionic liquid and at least one aryl alkyl ionic liquid.

The aryl alkyl ionic liquid includes but is not limited to 1-benzyl, 3-methyl imidazolium bromide; 1-benzyl, 3-methyl imidazolium chloride; 1-benzyl, 3-methyl imidazolium acetate; 1-benzyl, 3-methyl imidazolium methane sulfonate; 1-benzyl, 3-methyl imidazolium phosphate; Benzyl tributyl phosphonium bromide, Benzyl tributyl ammonium bromide; 1-phenyl, 3-methyl imidazolium chloride; 1-phenyl, 3-methyl imidazolium bromide; 1-phenyl, 3-methyl imidazolium acetate; 1-phenyl, 3-methyl imidazolium methane sulfonate; 1-phenyl, 3-methyl imidazolium phosphate; Phenyl tributyl phosphonium bromide; Phenyl tributyl ammonium bromide; 1,3-dibenzyl imidazolium chloride; 1,3-dibenzyl imidazolium bromide; 1,3-dibenzyl imidazolium acetate; 1,3-dibenzyl imidazolium methane sulfonate; and 1,3-dibenzyl imidazolium phosphate.

The alkyl ionic liquid includes but is not limited to 1-butyl, 3-methyl imidazolium bromide; 1-butyl, 3-methyl imidazolium chloride; 1-butyl, 3-methyl imidazolium acetate; 1-butyl, 3-methyl imidazolium methane sulfonate; 1-butyl, 3-methyl imidazolium phosphate; 1-ethyl, 3-methyl imidazolium chloride; 1-ethyl, 3-methyl imidazolium bromide; 1-ethyl, 3-methyl imidazolium acetate; 1-ethyl, 3-methyl imidazolium methane sulfonate; 1-ethyl, 3-methyl imidazolium phosphate; Tetrabutyl phosphonium chloride; Tetrabutyl phosphonium bromide; Tetrabutyl phosphonium acetate; Tetrabutyl phosphonium methane sulfonate; Tetrabutyl phosphonium phosphate; Trihexyl Tetradecyl phosphonium chloride; Trihexyl Tetradecyl phosphonium bromide; Trihexyl Tetradecyl phosphonium acetate; Trihexyl Tetradecyl phosphonium decanoate; Tetrabutyl ammonium chloride; Tetrabutyl ammonium bromide; Tetrabutyl ammonium acetate; Tetrabutyl ammonium methane sulfonate; Tetrabutyl ammonium phosphate; Choline chloride; Choline bromide; choline acetate; and choline methane sulfonate.

The catalyst employed in the composition of the present disclosure comprises at least one metal compound, the metal being selected from the group consisting of cobalt, magnesium, chromium, copper, nickel, vanadium, iron, molybdenum, tin, cerium, zirconium, cesium and titanium. In one embodiment the catalyst includes but is not limited to cobalt acetate, manganese acetate, cerium acetate, potassium acetate, cesium acetate, zirconium acetate, copper acetate, cobalt oxalate, manganese oxalate, cerium oxalate, potassium oxalate, cesium oxalate, zirconium oxalate and copper oxalate.

The present disclosure is further illustrated herein below with the help of the following examples. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

EXAMPLES

A: Comparative Examples (1 to 5)

Preparation of Mixtures which are Devoid of p-Toluic Acid and their Oxidation

Procedure

Oxidation of p-xylene was carried out at 215° C. and 20-40 bar pressure using a mixture of acetic acid and ionic liquid with or without HBr in the presence of cobalt acetate and manganese acetate as catalyst.

The composition of each mixture is provided in table No. 1.

TABLE NO. 1

| Without p-Toluic acid | | | | |
|---|---|---|---|---|
| Example 1 | Example 2 | Example 3 | Example 4 | Example 5 |
| p-xylene (81.83 grams) | p-xylene (81.83 grams) | p-xylene (69.9 grams) | p-xylene (81.83 grams) | p-xylene (81.83 grams) |
| acetic acid (416.07 grams) | acetic acid (265.88 grams) | acetic acid (282.6 grams) | acetic acid (327.6 grams) | acetic acid (327.6 grams) |
| cobalt acetate•4H$_2$O (0.63 grams) | cobalt acetate•4H$_2$O (3.3 grams) | cobalt acetate•4H$_2$O (2.8 grams) | cobalt acetate•4H$_2$O (3.5 grams) | cobalt acetate•4H$_2$O (3.5 grams) |
| manganese acetate•4H$_2$O (0.89 grams) | manganese acetate•4H$_2$O (2.5 grams) | manganese acetate•4H$_2$O (2.1 grams) | manganese acetate•4H$_2$O (2.5 grams) | manganese acetate•4H$_2$O (2.5 grams) |
| 48% HBr (0.58 grams) | 1-butyl, 3-methyl imidazolium chloride (35%) (143.17 grams) + 48% HBr (3.3 grams) | 1-butyl, 3-methyl imidazolium methane sulfonate (33%) (139.8 grams) + 48% HBr (2.8 grams) | Tetra butyl phosphonium bromide (20%) (81.83 grams) | Tetra butyl phosphonium bromide (81.83 grams) + 48% HBr (2.8 grams) |
| Temperature (° C.): 215 | Temperature (° C.): 215 | Temperature (° C.): 215 | Temperature (° C.): 215 | Temperature (° C): 215 |
| Pressure (Bar): 40 | Pressure(Bar): 40 | Pressure(Bar): 40 | Pressure(Bar): 40 | Pressure (Bar): 40 |
| Time (hours): 3 | Time (hours): 3 | Time (hours): 3 | Time (hours): 3 | Time (hours): 3 |
| Intermediate (4-CBA) content: 5600 ppm | Intermediate (4-CBA) content: 91000 ppm | Intermediate (4-CBA) content: 85000 ppm | Intermediate (4-CBA) content: 19000 ppm | Intermediate (4-CBA) content: 42000 ppm |

B: Examples (6 to 10)

Preparation of Mixtures which Essentially Contains p-Toluic Acid and their Oxidation Procedure Oxidation of p-xylene was carried out at 215° C. and 20-40 bar pressure using a mixture of p-Toluic acid, acetic acid and ionic liquid with or without HBr in the presence of cobalt acetate and manganese acetate as catalyst.

The composition of each mixture is provided in table No. 2.

TABLE NO. 2

| With p-Toluic acid | | | | |
|---|---|---|---|---|
| Example 6 | Example 7 | Example 8 | Example 9 | Example 10 |
| p-xylene (74.04 grams) acetic acid (327.38 grams) cobalt acetate•4H$_2$O (0.63 grams) manganese acetate•4H$_2$O (0.89 grams) 1-butyl, 3-methyl imidazolium acetate (81.83 grams) | p-xylene (74.04 grams) acetic acid (327.38 grams) cobalt acetate•4H$_2$O (0.63 grams) manganese acetate•4H$_2$O (0.89 grams) 1-butyl, 3-methyl imidazolium acetate (81.83 grams) + 48% HBr (5.23 grams) | p-xylene (77.93 grams) acetic acid (315.71 grams) cobalt acetate•4H$_2$O (0.63 grams) manganese acetate•4H$_2$O (0.89 grams) tetra butyl phosphonium bromide (20.91 grams) + 1-butyl, 3-methyl imidazolium acetate (78.93 grams) | p-xylene (77.93 grams) acetic acid (315.13 grams) cobalt acetate•4H$_2$O (0.63 grams) manganese acetate•4H$_2$O (0.89 grams) tetra butyl phosphonium bromide (20.91 grams) + 1-butyl, 3-methyl imidazolium acetate (78.93 grams) + 48% HBr (0.58 grams) | p-xylene (81.83 grams) acetic acid (411.07 grams) cobalt acetate•4H$_2$O (0.63 grams) manganese acetate•4H$_2$O (0.89 grams) 48% HBr (0.58 grams) |
| p-Toluic acid: 2% (10 grams) Temperature (° C.): 215 Pressure (Bar): 40 Time (hours): 3 No terephthalic acid formed | p-Toluic acid: 2% (10 grams) Temperature (° C.): 215 Pressure(Bar): 40 Time (hours): 3 Intermediate (4-CBA) content: 5600 ppm | p-Toluic acid: 1% (5 grams) Temperature (° C.): 215 Pressure(Bar): 40 Time (hours): 3 Intermediate (4-CBA) content: 1600 ppm | p-Toluic acid: 1% (5 grams) Temperature (° C.): 215 Pressure(Bar): 40 Time (hours): 3 Intermediate (4-CBA) content: 8700 ppm | p-Toluic acid: 1% (5 grams) Temperature (° C.): 215 Pressure(Bar): 40 Time (hours): 3 Intermediate (4-CBA) content: 5600 ppm |

From the results as shown in tables 1 and 2, it is clear that incorporation of external p-Toluic acid reduces the 4-carboxy-benzaldehyde (4-CBA) content in terephthalic acid.

Particularly, it is found that when a mixture/composition containing p-Toluic acid and ionic liquid is used during the oxidation of p-xylene, there is significant reduction in formation 4-CBA. Example 8 clearly shows that the formation of 4-CBA is reduced to 1600 ppm i.e. the formation of 4-CBA is 3.5 times less than the conventional process for preparation of terephthalic acid. This in turn suggests that the mixture of the present disclosure is capable of producing terephthalic acid in a highly pure form.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "a", "at least" or "at least one" suggests the use of one or more elements or ingredients or quantities, as the use may be in the embodiment of the disclosure to achieve one or more of the desired objects or results.

The numerical values given for various physical parameters, dimensions and quantities are only approximate values and it is envisaged that the values higher or lower than the numerical value assigned to the physical parameters, dimensions and quantities fall within the scope of the disclosure and the claims unless there is a statement in the specification to the contrary.

While certain embodiments of the disclosure have been described, these embodiments have been presented by way of examples only, and are not intended to limit the scope of the disclosure. Variations or modifications in the composition of this disclosure, within the scope of the disclosure, may occur to those skilled in the art upon reviewing the disclosure herein. Such variations or modifications are well within the spirit of this disclosure.

The invention claimed is:

1. A composition for preparing terephthalic acid; said composition consisting essentially of:
   i. p-Toluic acid in an amount of 0.05% to 4% with respect to the total mass of the composition;
   ii. at least one catalyst in an amount of 0.02% to 2.5% with respect to the total mass of the composition;
   iii. at least one ionic liquid in an amount of 0.04% to 50% with respect to the total mass of the composition;
   iv. at least one carboxylic acid solvent; and
   v. p-xylene,
   said composition when used in the preparation of terephthalic acid, results in the formation of less than 2000 ppm of 4-carboxy-benzaldehyde (4-CBA).

2. The composition as claimed in claim 1, wherein the proportion of the ionic liquid to the carboxylic acid solvent ranges between 1:1 and 1:20.

3. The composition as claimed in claim 1, wherein the ionic liquid is at least one selected from the group consisting of alkyl ionic liquids and aryl alkyl ionic liquids.

4. The composition as claimed in claim 1, wherein the ionic liquid comprises an organic cation selected from the group consisting of quaternary ammonium, cholinium, sulfonium, phosphonium, guanidinium, imidazolium, pyridinium, pyrrolidinium, morpholinium, quinolinium, isoquinolinium, pyrazolium and piperidinium; and an anion selected from the group consisting of chloride, bromide, fluoride, iodide, mesylate, tosylate, hydrogen sulfate, sulfate, alkyl sulfonate, phosphates, phosphonates, akyl phosphates, nitrates, nitrites, carbonates, acetates, bicarbonates, hydroxides and oxides.

5. The composition as claimed in claim 1, wherein the ionic liquid comprises a combination of at least one alkyl ionic liquid and at least one aryl alkyl ionic liquid.

6. The composition as claimed in claim 1, wherein the catalyst comprises at least one metal compound, the metal being selected from the group consisting of cobalt, magnesium, chromium, copper, nickel, vanadium, iron, molybdenum, tin, cerium, zirconium, cesium and titanium.

7. The composition as claimed in claim 1, wherein the catalyst is at least one selected from the group consisting of cobalt acetate, manganese acetate, cerium acetate, potassium acetate, cesium acetate, zirconium acetate, copper acetate, cobalt oxalate, manganese oxalate, cerium oxalate, potassium oxalate, cesium oxalate, zirconium oxalate and copper oxalate.

8. The composition as claimed in claim 1, wherein the carboxylic acid solvent is acetic acid.

9. A process for preparing terephthalic acid; said process consisting essentially of the following steps:

preparing a composition comprising p-Toluic acid in an amount of 0.05% to 4% with respect to the total mass of the composition; at least one catalyst in an amount of 0.02% to 2.5% with respect to the total mass of the composition; at least one ionic liquid in an amount of 0.04% to 50% with respect to the total mass of the composition; at least one carboxylic acid solvent and p-xylene; and oxidizing said composition in the presence an oxidizing agent selected from the group consisting of oxygen and air, at a temperature of 100 to250° C. and at a pressure of 10 to 60 bar to obtain terephthalic acid, the content of 4-carboxy-benzaldehyde (4-CBA) being less than 2000 ppm.

* * * * *